United States Patent [19]  [11]  4,116,976
Englander et al.  [45]  Sep. 26, 1978

[54] METHOD OF PREPARING PHTHALIDE

[75] Inventors: Fritz Englander, Bonn-Bad Godesberg; Jurgen Amort, Troisdorf, both of Germany

[73] Assignee: Dynamit Nobel Aktiengesellschaft, Troisdorf Bez. Koeln, Germany

[21] Appl. No.: 783,575

[22] Filed: Apr. 1, 1977

[30] Foreign Application Priority Data

Apr. 2, 1976 [DE] Fed. Rep. of Germany ....... 2614294

[51] Int. Cl.$^2$ ........................................... C07D 307/88
[52] U.S. Cl. ........................................... 260/343.3 R
[58] Field of Search ................................ 260/343.3 R

[56] References Cited

U.S. PATENT DOCUMENTS 2,114,696  3/1935  Austin et al. ................ 260/343.3 R Primary Examiner—Natalie Trousoe
Assistant Examiner—Jane T. Fan
Attorney, Agent, or Firm—Burgess, Dinklage & Sprung

[57] ABSTRACT

Method of preparing phthalide by hydrogenolysis of 3-chlorophthalide in the presence of a nobel metal catalyst, wherein hydrogenolysis is carried out in the absence of HCl acceptor.

The phthalide which is produced is a valuable chemical intermediate for the manufacture of dyes, plant protecting agents and pharmaceuticals.

8 Claims, No Drawings

METHOD OF PREPARING PHTHALIDE

BACKGROUND

The subject of the present invention is a method of preparing phthalide, in which 3-chlorophthalide is subjected to a hydrogenolysis in the presence of hole metal catalysts.

The exchange of hydrogen for organically bound halogen, hereinafter to be referred to as hydrogenolysis, in the presence of palladium, platinum or nickel catalysts, is known. In this process, aromatically bound halogen is more easily substituted than aliphatically bound halogen. In all cases, the less acid the reaction solution is, the more easily the reaction takes place. However, since hydrogen chloride is liberated in the hydrogenolysis, it is common practice to add known hydrogen chloride acceptors to the reaction mixture to increase the speed of reaction and the volume-time yields.

The addition of acid-binding compounds, such as, for example, amines, sodium acetate, and alkali-containing methanol, has, however, the disadvantage that the working up of the reaction product and of the catalyst is thereby made considerably more difficult. In particular, the reprocessing of the catalyst important to the process is possible only by means of a plurality of steps, so that a procedure of this kind is not technically feasible.

Another possibility of intercepting the hydrochloric acid that is formed would consist in performing the hydrogenolysis in the presence of a solvent having a high ability to dissolve hydrogen chloride. A solvent of this kind for the hydrogenolysis of benzyl chloride to toluene is, for example, methanol.

If this procedure of hydrogenolysis in the presence of methanol is to be applied to the preparation of phthalide from 3-chlorophthalide, however, the following disadvantages are apparent: The primarily forming phthalide reacts immediately with the hydrochloric acid in the solution to cleave the lactone ring further to o-chloromethylbenzoic acid, which further reacts with excess methanol present to form toluylic acid methyl ester, so that this ester develops in this procedure as one of the main products, while phthalide is produced in a yield of only 15 to 18%.

Even if 3-chlorophthalide is subjected to the hydrogenolysis at, for example, 140° C., under pressure, in the absence of methanol, the above-mentioned lactone cleavage occurs, the chloromethyl group being further degraded to the methyl group, so that the reaction mixture consists mainly of toluylic acid and not much phthalide.

The problem thus existed of performing the hydrogenolysis of 3-chlorophthalide such that the formation of undesired by-products would be suppressed and so that yields of phthalide greater than 90% would be obtained.

THE INVENTION

As a solution of this problem a method has now been found for the preparation of phthalide by the hydrogenolysis of 3-chlorophthalide in the presence of noble metal catalysts, which is characterized in that the hydrogenolysis is performed in the absence of HCL acceptors at temperatures between about 50° and about 250° C., preferably between about 80° and about 130° C..

It has surprisingly been found that, under the above-specified temperature conditions, especially in the preferred temperature range, the developing hydrogen chloride, during the time it is present in the reaction mixture, enters into secondary reactions only to a minor extent. Also, within the specified temperature range the acid reaction medium that establishes itself has only a small influence on the speed of the reaction.

The hydrogen is added in such amounts that it bubbles through the reaction mixture. The rate of flow amounts desirably to at least 60 liters (at 25° C. and 760 Torr) per liter of reaction mixture. However, larger rates of flow can also be used. The hydrogen does not need to be especially purified, and therefore it can be of a technical grade of purity.

The procedure of the invention has the advantage that the catalyst does not have to be reprocessed, since in this procedure no insoluble chlorine compounds are formed. In a batch process, the catalyst, after separation from the reaction product, can immediately be reused for the next batch without being subjected to any special refining operation. Even after use in more than 20 batches, the activity of the catalyst is diminished hardly at all.

The amount of the catalyst is about 0.1 to about 10 percent by weight, preferably, about 2.0 to about 5.0 percent by weight with respect to the 3-chlorophthalide put in. Suitable catalysts are the noble metals in the Eight Group of the 5th and 6th Periods of the Periodic System, which are also referred to as platinum metals, examples being rhodium, ruthenium or phatinum. The metal is used on a support, the support containing, say, 5% of the metal. It is also possible, however, to use support material of a higher or lower metal content. Examples of support material are charcoal, aluminum oxide, barium sulfate or kieselgur. The above-stated amount of catalyst refers to the amount to be used of the catalyst support containing the platinum metal.

The reaction can be performed either with or without solvent. Suitable solvents are especially those compounds which boil above about 80° C. and in which hydrogen chloride is soluble to only a very slight degree. The solvents must, of course, be inert with respect to 3-chlorophthalide and phthalide and capable of dissolving these compounds to a sufficient degree. Examples of suitable solvents are aromatic hydrocarbons such as, for example, toluene and xylene.

If the reaction is performed in the absence of solvents, it must be conducted at temperatures above the melting point of phthalide. It is preferred, then, to operate at temperatures between about 80° C. and about 100° C..

The reaction vessel is preferably an elongated, upstanding vessel to which hydrogen is fed from the bottom in finely distributed form. Also suitable, however, are reaction vessels which assure the distribution of the introduced hydrogen throughout its entire content. The injection hydrogen is to stir up the catalyst contained in the reaction medium insofar as possible. In an elongated, upright reaction vessel, the reaction medium forms with the catalyst stirred up therein a column of hydrogen bubbles.

The hydrogen is fed into the vessel until no more hydrogen chloride escapes. The testing for hydrogen chloride is performed in the gas mixture escaping from the reactor, which consists of excess hydrogen plus the hydrogen chloride that forms during the reaction and is expelled.

After the reaction has ended, the catalyst is separated from the reaction mixture and the phthalide is separated in a known manner by distillation and/or crystallization.

The phthalide which is produced is a valuable chemical intermediate for the manufacture of dyes, (e.g. derivates of anthrachinone) or 3-bromo phthalide, which is used to introduce the phthalidyl-group in antibiotics (e.g. U.S. Pat. Nos. 3,860,579, 3,919,196, 3,939,180, 3,963,702 and 3,963,704). Furthermore phthalide is used as a plasticizer for nitrocellulose.

EXAMPLES

EXAMPLE 1

842.5 weight-parts of 3-chlorophthalide are dissolved in 750 parts of toluene in a bubble tube 65 cm long and 6.5 cm in diameter, in the middle of which there is centered an introduction tube with perforated metal plates mounted thereon, which is set in vibration by means of a vibrator. Also contained in the tube are 25.3 parts of a catalyst consisting of a support mass of aluminum oxide carrying 5% of metallic palladium. At a temperature of 85° C., hydrogen is introduced from above through the introduction tube located in the center of the bubble tube, at a rate of 120 liters per hour. The hydrogen emerges from the bottom of the introduction tube and rises through the holes in the perforated metal plates.

The exhaust gas composed of unreacted hydrogen and hydrogen chloride flows, after separation of the solvent vapors in a reflux condenser, into a receiver in which a pH of 7 is maintained by the continuous addition of adjusted soda lye, so that in this manner the transformation can be determined at any time.

After 6.25 hours, 99.8% of the theoretically possible HCl has been split off and the evolution of hydrogen chloride ceases. The solution is separated from the catalyst and cooled to −10° C. 604 parts of phthalide are obtained (90.1% of the theory). The melting point is at 72–73° C.. The gas-chromatographic purity is 99%.

By processing the mother liquor, another 40 parts of phthalide were obtained melting at 69–72° C. and having a purity of 98%.

EXAMPLE 2

As in Example 1, 842.5 weight-parts of 3-chlorophthalide were dissolved in 750 parts of xylene and 25.3 parts of catalyst composed of 5% Pd on $Al_2O_3$ were added; at a temperature of 115° C., 180 liters of hydrogen were fed in per hour. After 1¾ hours, 98% of the theoretically possible HCl has been split off. Hydrogen was introduced for another 30 minutes, whereupon the transformation increased to 99.5% of the theory.

After separation of the catalyst the mixture was distilled. After a first running of xylene, phthalide was distilled off at a pressure of 0.1 Torr and a temperature of 103–106° C..

Yield: 610 parts by weight (91% of the theory), with a content of 99.8% phthalide.

EXAMPLE 3

824.5 weight parts of 3-chlorophthalide were melted at 85° C. in an autoclave, 25.3 parts of catalyst (5% Pd on $BaSo_4$), and a hydrogen stream of 180 l/h was introduced with vigorous agitation. The excess hydrogen and the hydrogen chloride that evolved were removed as in the above examples. After 8½ hours, the evolution of hydrogen chloride ceased. The melt was separated from the catalyst. In the distillation that followed, 608 weight-parts of phthalide were obtained (90.7% of the theory) having a content of 99.6% phthalide.

EXAMPLE 4

842.5 parts of 3-chlorophthalide and 750 parts of xylene were heated in a stirring vessel with 25.3 parts of a catalyst composed of 5% Pt on charcoal, at 85° C., and 160 liters of hydrogen were fed in hourly. After a reaction time of 13 hours, hydrogen chloride ceased to evolve. The reaction mixture was separated from the catalyst and worked up by distillation. 549 parts of phthalide were obtained, corresponding to 81.9% of the theory.

EXAMPLE 5

In an apparatus identical to that of Example 1, 842.5 parts of 3-chlorophthalide and 750 parts of a catalyst composed of 5% Pd on $Al_2O_3$ and 180 liters of hydrogen were fed in per hour at a temperature of 85° C.. As soon as the evolution of hydrogen chloride stopped, the catalyst was removed by filtration and the phthalide was separated by crystallization.

The separated catalyst was returned without further purification to the apparatus together with 842.5 parts of 3-chlorophthalide and 750 parts of toluene, and the reaction was performed again under the same conditions as before.

This procedure was repeated a number of times. From the list below it will be seen that the catalyst does not lose its activity even after a great number of batches. Instances of slight prolongations of the reaction time are probably attributable to losses of catalyst occurring when the catalyst is separated. Making up such losses by the addition of small amounts of fresh catalyst restores the original reaction time.

| No. | Reaction time in hours | Phthalide yield in % of theory | Remarks |
| --- | --- | --- | --- |
| 1 | 5.5 | 94.5 | |
| 2 | 6.25 | 91.6 | |
| 3 | 6.0 | 90.1 | |
| 4 | 5.3 | 90.0 | |
| 5 | 6.3 | 88.4 | |
| 6 | 7.0 | 90.1 | |
| 7 | 7.2 | 92.0 | |
| 8 | 7.5 | 93.2 | |
| 9 | 7.9 | 92.1 | |
| 10 | 5.5 | 93.0 | Addition of 2.0 parts of fresh catalyst. |
| 11 | 5.0 | 94.1 | |
| 12 | 5.5 | 92.7 | |
| 13 | 5.7 | 94.6 | |
| 14 | 5.9 | 95.0 | |
| 15 | 6.0 | 93.0 | |
| 16 | 6.5 | 92.5 | |
| 17 | 6.8 | 93.8 | |
| 18 | 7.0 | 90.0 | |
| 19 | 7.5 | 91.1 | |
| 20 | 7.7 | 89.2 | |
| 21 | 6.0 | 90.0 | Addition of 1.5 parts of fresh catalyst |
| 22 | 5.8 | 93.4 | |

Here the series was discontinued, even though the catalyst still had not lost its activity.

What is claimed is:

1. Process of preparing phthalide which comprises contacting 3-chlorophthalide with hydrogen in the presence of noble metal catalyst, at between about 50° and about 250° C. in the absence of HCL acceptors, for hydrogenolysis of the 3-chlorophthalide.

2. Method of claim 1 wherein the hydrogenolysis is performed at temperatures between about 80° and about 130° C..

3. Method of claim 1 wherein the hydrogenolysis is performed in the presence of an inert organic solvent.

4. Method of claim 3 wherein the inert organic solvent is an aromatic hydrocarbon solvent.

5. Method of claim 2 wherein the hydrogenolysis is performed in the presence of an inert organic solvent.

6. Method of claim 5 wherein the inert organic solvent is an aromatic hydrocarbon solvent.

7. Method of claim 2 wherein the hydrogenolysis is performed in the absence of a solvent.

8. Method of claim 7 wherein the hydrogenolysis is performed at temperatures between about 80° C. and about 100° C.

* * * * *